United States Patent [19]

McRae

[11] Plant 4,176

[45] Jan. 3, 1978

[54] LILY PLANT: LILIUM 'FIREBRAND'

[75] Inventor: Edward A. McRae, Boring, Oreg.

[73] Assignee: Melridge, Inc., Gresham, Oreg.

[21] Appl. No.: 761,227

[22] Filed: Jan. 21, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant, single stemmed, tall, and stately, with deep green leaves. The plant has numerous buds having a deep red color when the tepals divide and unfurl. The buds develop into upright flowers of fine form and substance with exceptionally broad tepals and an attractive deep red color. Both plant and flower are characterized by high disease resistance and high tolerance of infection by virus.

1 Drawing Figure

BACKGROUND OF THE INVENTION

My new variety of lily plant originated as a seedling selected from a group of seedlings at Gresham, Oreg. The seedlings were planted during a breeding program carried on by me since the year 1966. This program had as its primary objective the production of upright hybrid Asiatic lilies in the red color shades and characterized by plant vigor, rapid propagation, high resistance to disease, tolerance of infection by virus, having flowers of superior form and color.

I achieved the desired objective by using as the seed parent Lilium X 'Harmony' clone and as the pollen parent Lilium X 'Byam's Ruby'.

My new lily plant is single stemmed, tall and stately in form, and has vigorous growth and propagation characteristics. Its stems are dark in color and provide an attractive contrast to the abundant foliage which is deep green in color with a reddish cast.

The plant has a large number of buds, producing from 6 to 12 from a bulb 5 to 7 inches in circumference. The buds are an attractive deep red color when the tepals first divide, and this color intensifies when the tepals begin to unfurl.

The flowers are particularly distinctive. They are characterized by tepals of fine form, unusual breadth, and sharp clean outline. They are lightly spotted, primarily at the base, and are an intense, vibrant, deep red color.

The plant is one of the most vigorous upright Asiatic lilies yet produced. It is a rapid propagator, and has superb disease resistance and a high degree of tolerance of infection by virus. It is an excellent garden lily and satisfactory for use in the cut flower or pot plant trade by forcing precooled bulbs, all as observed at Gresham, Oreg.

My new variety of lily plant has been asexually reproduced by me and under my direction at Gresham, Oreg. Successive generations produced by bulb scale propagation and natural propagation from bulblets have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing which shows the plant, its stem and foliage, its buds in their various stages of development, and the open bloom in full color. Also shown is the tepal arrangement, the great width of the tepals, the connection of the flower to the stalk, and particularly the rich red color of the flower.

DESCRIPTION OF THE NEW VARIETY

The following is a detailed description of my new variety of Asiatic hybrid lily, with nomenclature according to *The International Lily Register* (Royal Horticultural Society, London, 2nd edition, 1969,) and with color designations according to the Royal Horticultural Society Color Chart, published by the Royal Horticultural Society in 1966.

THE PLANT

Origin: Seedling.

Parentage:

- *Seed parent.*—Lilium X 'Harmony' (unpatented).
- *Pollen parent.*—Lilium X 'Byam's Ruby' (unpatented).

Classification:

- *Botanic.*—Hybrid Lilium cultivar; Division I-A of the Horticultural Classification of Lilies of the R.H.S.
- *Commercial.*—Asiatic hybrid lily.

Form: Single stem, tall and stately.

Height: 25 to 30 inches from bulbs of average size.

Growth: Very vigorous and upright with exceptional strength.

Foliage:

- *Quantity.*—Abundant.
- *Size of leaf.*—3 to 4 inches long.
- *Shape of leaf.*—Lanceolate.
- *Texture.*—Glossy.
- *Color.*—Deep green with reddish cast on both upper and under sides.

Bulbs:

- *Size.*—Any size, ranging up to about 12 inches in circumference.
- *Color.*—White, with a reddish cast when exposed to light.

THE BUD

Form: Obtuse; urn-shaped and long.

Size: About 1.5 inches long and about 1.5 inches in circumference, increasing as bud develops.

Opening: Bud opens slowly.

Color: Deep red when tepals first divide. The deep red color intensifies when the tepals begin to unfurl.

Tepals: The tepals curl back. They are deep red on the inside and deep red on the outside.

Peduncle: About 2 inches long; hairy; erect; deep green in color.

THE FLOWER

Blooming habit: Recurrent. Annually in mid season. Blooms once and profusely.

Size: Medium; about 5 inches in diameter.

Borne: In clusters, from 6 to 12 on a single stem, from a bulb 5 to 7 inches in circumference.

Shape: Cup shaped, without substantial change in form with age. The tepals reflex back only slightly as the bloom matures.

Tepalage:

*Number of tepals.*—6.

*Arrangement.*—Imbricated.

*Color.*—White at the base. The outer tepal, inside tepal, and reverse side of the tepal are all deep red, R.H.S. C.C.34A through B, fading to R.H.S. C.C.42A as the bloom grows older.

*Tepal longevity.*—Tepals stay on the stem about 3 weeks.

*Spotting.*—Lightly spotted with small spots at the base of the tepals.

Pedicel:

*Length.*—About 2 inches.

*Color.*—Deep green.

*Form.*—Sturdy and upright.

Color change: The red color of the flower changes to a still deeper red after full bloom.

Appearance: The flower is shiny.

Disease resistance: The flower and plant are highly resistant to disease; in particular, they are resistant to Fusarium and Botrytis.

Fragrance: The flower is not fragrant.

Lasting quality: The flower is long lasting on the plant and exceptionally long lasting as a cut flower.

THE REPRODUCTIVE ORGANS

Stamens, anthers:

*Arrangement.*—Typical of Liliaceae.

*Length.*—About 2 inches.

*Number.*—6.

*Filaments.*—Length, about 2 inches; color, cream and reddish at tip.

Pollen and anthers: Dark reddish-brown in color.

Pistils: One in number with a length of about 2 inches.

Stigma: Deepest purple in color.

Characteristics of ovaries: Typical of genus Lilium.

FRUIT

Fertility: The fruit is fertile.

Shape: The fruit is ovoid.

Color at maturity: The fruit is soft brown.

My new variety of Asiatic hybrid lily most nearly resembles the variety 'Cinnabar' (unpatented) but is distinguished therefrom by its superiority in form, vigor, growth characteristics, resistance to disease, the clear, sharp form of its flowers with their exceptionally broad tepals, by its greater number of flowers, and in particular by the intense, deep red color of its flowers.

I claim:

1. A new and distinctive variety of Asiatic hybrid lily plant substantially as herein shown and described, characterized by its tall, stately and erect growth, the great vigor of its growth, its strong dark-colored stem, its abundant deep green foliage, its numerous buds colored deep red when the tepals first divide and unfurl, the fine form and texture of the flowers, the exceptionally broad tepals, the distinctive vibrant deep red color of the flowers, its rapid propagation characteristics, its superb disease resistance, its high tolerance to virus, and its suitability for use both as a garden flower and as a cut flower produced by forcing precooled bulbs.

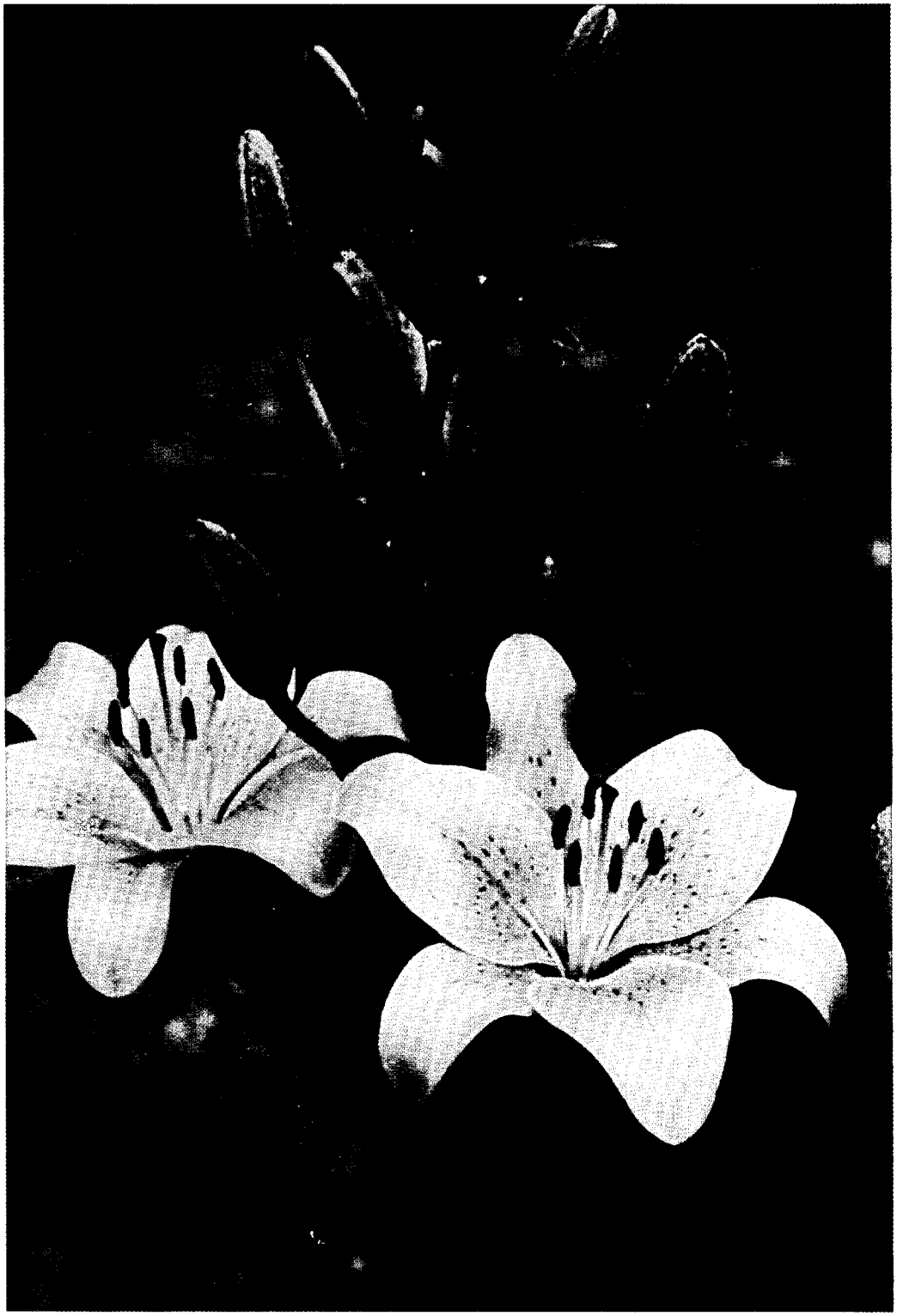

* * * * *